(12) United States Patent
Palin et al.

(10) Patent No.: US 11,911,127 B2
(45) Date of Patent: Feb. 27, 2024

(54) STORING A SIGNAL TO A MEMORY (71) Applicant: Nokia Technologies Oy, Espoo (FI)

(72) Inventors: Arto Palin, Akaa (FI); Jukka Pekka Reunamaki, Tampere (FI)

(73) Assignee: NOKIA TECHNOLOGIES OY, Espoo (FI)

(*) Notice: Subject to any disclaimer, the term of this patent is extended or adjusted under 35 U.S.C. 154(b) by 578 days.

(21) Appl. No.: 16/767,768

(22) PCT Filed: Dec. 4, 2018

(86) PCT No.: PCT/EP2018/083455
§ 371 (c)(1),
(2) Date: May 28, 2020

(87) PCT Pub. No.: WO2019/120977
PCT Pub. Date: Jun. 27, 2019

(65) Prior Publication Data
US 2020/0359894 A1 Nov. 19, 2020

(30) Foreign Application Priority Data
Dec. 22, 2017 (EP) .................................. 17210501

(51) Int. Cl.
*A61B 5/00* (2006.01)
*A61B 5/352* (2021.01)
(52) U.S. Cl.
CPC ............ *A61B 5/0006* (2013.01); *A61B 5/352* (2021.01); *A61B 5/6831* (2013.01);
(Continued)

(58) Field of Classification Search
CPC ..... A61B 5/0006; A61B 5/352; A61B 5/6831; A61B 5/7221; A61B 5/7246;
(Continued)

(56) References Cited

U.S. PATENT DOCUMENTS 5,263,486 A 11/1993 Jeffreys
5,355,891 A * 10/1994 Wateridge .............. A61B 5/335
600/521
(Continued)

FOREIGN PATENT DOCUMENTS

EP 3094244 A1 11/2016
WO 2015/107266 A1 7/2015
WO 2017/120560 A1 7/2017

OTHER PUBLICATIONS

Office action received for corresponding Indian Patent Application No. 202047031199, dated Nov. 12, 2021, 8 pages of office action.
(Continued)

*Primary Examiner* — Rex R Holmes
(74) *Attorney, Agent, or Firm* — SQUIRE PATTON BOGGS (US) LLP (57) ABSTRACT

An apparatus comprising: circuitry configured to classify a signal; and circuitry configured to control saving of the signal to a memory with a conditional resolution, wherein a signal that is classified as anomalous is saved at higher resolution as a higher resolution signal and a signal that is not classified as anomalous is saved at lower resolution as a lower resolution signal or is not saved.

18 Claims, 4 Drawing Sheets

(52) U.S. Cl.
CPC .......... *A61B 5/7221* (2013.01); *A61B 5/7246* (2013.01); *A61B 5/7264* (2013.01)

(58) Field of Classification Search
CPC ...... A61B 5/7264; A61B 5/366; G16H 50/20; H03M 7/6094; H03M 7/30; H03M 7/3059; G06F 3/05
See application file for complete search history.

(56) References Cited

U.S. PATENT DOCUMENTS

| | | | |
|---|---|---|---|
| 7,933,658 B2* | 4/2011 | Corndorf | A61N 1/025 607/60 |
| 8,744,561 B2 | 6/2014 | Fahey | |
| 8,814,811 B2 | 8/2014 | Scholten et al. | |
| 2004/0193064 A1 | 9/2004 | Shusterman | |
| 2007/0142735 A1* | 6/2007 | Shin | A61B 5/30 600/509 |
| 2008/0252481 A1* | 10/2008 | Vacar | H04Q 9/00 340/870.38 |
| 2011/0082377 A1 | 4/2011 | Mahajan et al. | |
| 2012/0262303 A1* | 10/2012 | Fahey | A61B 5/14552 340/870.02 |
| 2015/0054654 A1 | 2/2015 | Albinali | |
| 2015/0313490 A1 | 11/2015 | Archer et al. | |

OTHER PUBLICATIONS

Office action received for corresponding European Patent Application No. 17210501.7, dated Feb. 24, 2021, 9 pages of office action.
Chandra et al., "Telecardiology: Hurst Exponent Based Anomaly Detection in Compressively Sampled Ecg Signals", IEEE 15th International Conference on e-Health Networking, Applications and Services, 2013, pp. 350-354.
Borowska, "Entropy-Based Algorithms in the Analysis of Biomedical Signals", Studies in Logic, vol. 43, No. 1, Dec. 2015, pp. 21-32.
Extended European Search Report received for corresponding European Patent Application No. 17210501.7, dated Jun. 7, 2018, 12 pages.
"Quantization (signal processing)", Wikipedia, Retrieved on May 26, 2020, Webpage available at : https://en.wikipedia.org/wiki/Quantization_(signal_processing).
"Audio bit depth", Wikipedia, Retrieved on May 26, 2020, Webpage available at : https://en.wikipedia.org/wiki/Audio_bit_depth.
International Search Report and Written Opinion received for corresponding Patent Cooperation Treaty Application No. PCT/EP2018/083455, dated Feb. 21, 2019, 15 pages.
"ECG: The Ultimate Guide", Neurosky, Retrieved on May 26, 2020, Webpage available at : http://neurosky.com/biosensors/ecg-sensor/ultimate-guide-to-ecg/.
European Examination Report issued in corresponding European Patent Application No. 17210501.7-1207 dated Jan. 12, 2023.

* cited by examiner

STORING A SIGNAL TO A MEMORY

RELATED APPLICATION

This application claims priority to PCT Application No. PCT/EP2018/083455, filed on Dec. 4, 2018, which claims priority to European Application No. 17210501.7, filed on Dec. 22, 2017, each of which is incorporated herein by reference in its entirety.

TECHNOLOGICAL FIELD

Embodiments of the present invention relate to storing a signal to a memory.

BACKGROUND

The accurate recording of a signal requires significant data.

The Nyquist-Shannon sampling theorem states that if a signal s(t) contains no frequencies higher than F Hz, it can be completely determined by sampling it at a rate of 2F samples/second.

Signals that contain high frequency components therefore require more samples and more memory to store the data.

If it is desirable to monitor a signal over an extended period of time, then the memory requirements for storing sufficient samples over the extended period of time can be very large.

The cost of such continuous, densely sampled data can be significant for storage, communication and processing, for example.

BRIEF SUMMARY

According to various, but not necessarily all, embodiments of the invention there is provided an apparatus comprising: circuitry configured to classify a signal; and circuitry configured to control saving of the signal to a memory with a conditional resolution, wherein a signal that is classified as anomalous is saved at higher resolution as a higher resolution signal and a signal that is not classified as anomalous is saved at lower resolution as a lower resolution signal or is not saved.

Therefore apparatus is configured to monitor the signal for anomalies. The signal only needs to be saved at the higher resolution when there is an anomaly. The existence of an anomaly may be determined by detecting the presence of an anomaly or by detecting the absence of normality.

In some but not necessarily all examples, the apparatus comprises: circuitry for quantizing the signal irrespective of classification into a number of significant bits, wherein the higher resolution signal is comprised of the number of significant bits including most significant bits and least significant bits, and wherein the lower resolution signal is comprised of a selected sub-set of the number of significant bits including most significant bits but not including least significant bits.

In some but not necessarily all examples, the apparatus comprises: circuitry for quantizing the signal irrespective of classification at a data rate, wherein the higher resolution signal comprises quantized samples at the data rate, and wherein the lower resolution signal comprises quantized samples selected at a rate less than the data rate.

In some but not necessarily all examples, the circuitry configured to classify a signal is configured to obtain a measure of similarity between the signal and a reference by comparison of the signal and the reference, wherein the signal is classified as an anomalous signal if it has a lower measure of similarity and is classified as a non-anomalous signal if it has a higher measure of similarity.

In some but not necessarily all examples, the circuitry configured to classify a signal is configured to obtain a measure of similarity between the signal and a reference by comparison of a portion of the signal and a portion of the reference, wherein the portion of the signal and the portion of the reference are determined from a comparison of the reference and the signal and the circuitry configured to control saving of the signal to a memory with a conditional resolution, is configured to save only the portion of the signal that is classified as anomalous at higher resolution. In some but not necessarily all examples, the circuitry configured to classify a signal is configured to compare the reference and the signal to determine the portion of the signal and the portion of the reference at a lower resolution than comparison of the signal and the reference to obtain the measure of similarity In some but not necessarily all examples, the circuitry configured to classify a signal is configured to determine the reference by comparison of each putative reference in a set of putative references with the signal, identifying the putative reference that best matches the signal as the reference.

In some but not necessarily all examples, the circuitry configured to classify a signal is configured to classify the signal in dependence upon a measure of quality of the signal.

In some but not necessarily all examples, the circuitry configured to control saving of the signal to a memory is configured to save the signal, when classified as anomalous, with a higher resolution that is dependent upon the quality of the signal.

In some but not necessarily all examples, the apparatus comprises: circuitry configured to compensate for movement artefacts affecting the signal.

In some but not necessarily all examples, the signal is a cyclic bio signal.

In some but not necessarily all examples, the apparatus comprises: the memory; a wireless transmitter, and data compression circuitry configured for data compression of the saved signal before wireless transmission of the compressed saved signal via the wireless transmitter.

In some but not necessarily all examples, the apparatus is configured as a personal computer device, wearable by a user. The apparatus comprises one or more sensors for sensing the signal, the memory and at least one processor for providing at least some of the circuitry.

According to various, but not necessarily all, embodiments of the invention there is provided a computer program, that when run on a processor, enables the processor to control: saving of a signal with conditional resolution in dependence upon a classification of the signal wherein an anomalous signal is saved at higher resolution as a higher resolution signal and a non-anomalous signal is saved at lower resolution as a lower resolution signal or not saved.

According to various, but not necessarily all, embodiments of the invention there is provided an apparatus comprising: means for classifying a signal; means for controlling saving of the signal with conditional resolution in dependence upon classification of the signal wherein an anomalous signal is saved at higher resolution as a higher resolution signal and a non-anomalous signal is saved at lower resolution as a lower resolution signal or not saved.

According to various, but not necessarily all, embodiments of the invention there is provided a method comprising: classifying a signal; controlling saving of the signal with conditional resolution in dependence upon classification of the signal, wherein an anomalous signal is saved at higher resolution as a higher resolution signal and a non-anomalous signal is saved at lower resolution as a lower resolution signal or not saved.

The following portion of this 'Brief Summary' section, describes various features that may be features of any of the embodiments described in the foregoing portion of the 'Brief Summary' section. The description of a function should additionally be considered to also disclose any means suitable for performing that function The signal may be processed in the same manner irrespective of classification. The higher resolution signal is then comprised of a larger number of significant bits including most significant bits and least significant bits of the processed signal. The lower resolution signal is comprised of a smaller number of significant bits including most significant bits but not including least significant bits of the processed signal.

In some but not necessarily all examples, the higher resolution signal is at a higher data rate and the lower resolution signal is at a lower data rate.

In some but not necessarily all examples, classifying a signal comprises obtaining a measure of similarity between the signal and a reference by comparison of the signal and the reference, wherein an anomalous signal has a lower measure of similarity and a non-anomalous signal has a higher measure of similarity.

In some but not necessarily all examples, the measure of similarity between the signal and the reference is obtained from a comparison of a portion of the signal and a portion of the reference, wherein the portion of the signal and the portion of the reference are determined from a comparison of the reference and the signal.

In some but not necessarily all examples, comparison of the reference and the signal to determine the portion of the signal and the portion of the reference is at a lower resolution than comparison of the signal and the reference to obtain the measure of similarity.

In some but not necessarily all examples, the reference is determined by comparison of each putative reference in a set of putative references with the signal to identify the putative references that best matches the signal as the reference.

According to various, but not necessarily all, embodiments of the invention there is provided an apparatus comprising: circuitry configured to classify a signal; and circuitry configured to control saving of the signal to a memory with a conditional resolution, wherein a signal that is classified as anomalous is saved at a resolution that is sufficient to classify the signal as anomalous and a signal that is not classified as anomalous is saved at a lower resolution as a lower resolution signal or is not saved. According to various, but not necessarily all, embodiments of the invention there is provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

Figure 1:
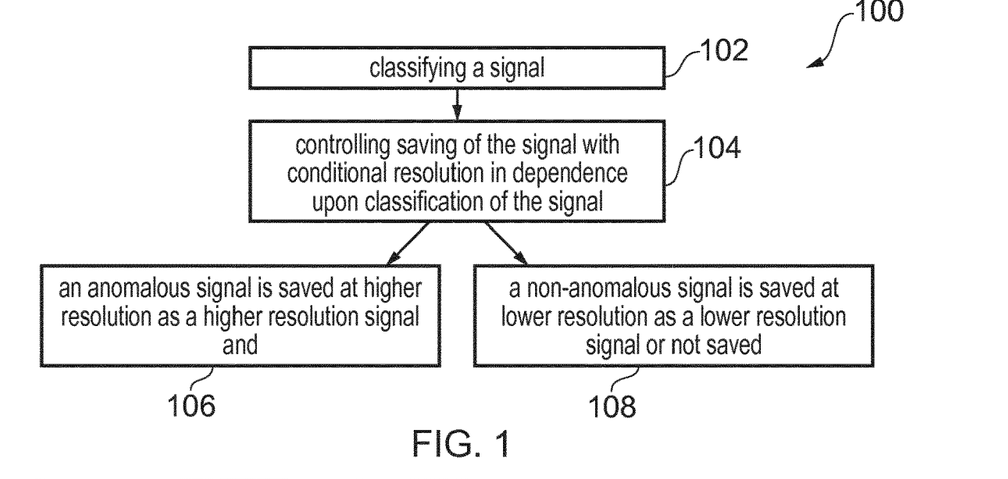
FIG. 1 illustrates an example of a method for controlling saving of a signal.

FIG. 1 illustrates an example of a method for controlling saving of a signal.

Figure 2A:
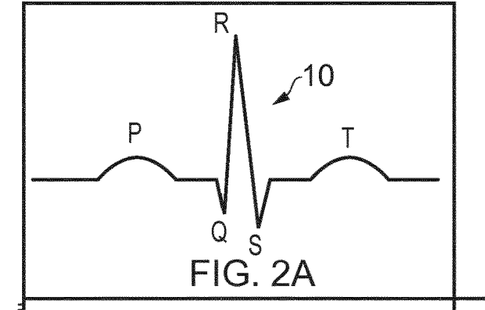
FIG. 2A illustrates an example of a signal.

The method 100, at block 102, comprises classifying a signal 10. An example of a signal is illustrated in FIG. 2A.

The method 100, at block 104, comprises controlling the saving of a signal 10 with conditional resolution in dependence upon classification of the signal 10. FIGS. 2B, 2C, 2D and 2E illustrate the signal 10 at different resolutions.

As a consequence of the method 100, an anomalous signal is saved at a higher resolution as a higher resolution signal and a non-anomalous signal is saved at a lower resolution as a lower resolution signal or not saved.

The method 100 is useful for monitoring a signal 10 for anomalies. The signal 10 only needs to be saved at the higher resolution when there is an anomaly. The existence of an anomaly may be determined by detecting the presence of an anomaly or the absence of normality.

FIG. 2A illustrates an example of a signal 10. In this example, the signal 10 is a bio-signal that is detected at a body of a subject. In this example, the bio-signal is an electrocardiogram (ECG) signal 10. The ECG signal 10 illustrated comprises a PQRST complex. This complex includes the slowly varying P-wave and T-wave either side of the rapidly varying QRS-wave. The ECG signal 10 is a cyclic signal in that it repeats and therefore comprises recurrent features. The ECG signal 10 is produced by the rapid polarization and depolarization of the heart and it is therefore repeated at each heartbeat.

Although an ECG signal 10 has been illustrated as an example of the signal 10, it is of course possible to use a large variety of other different signals 10. The invention is by no means limited to use with an ECG signal.

Figure 2B:
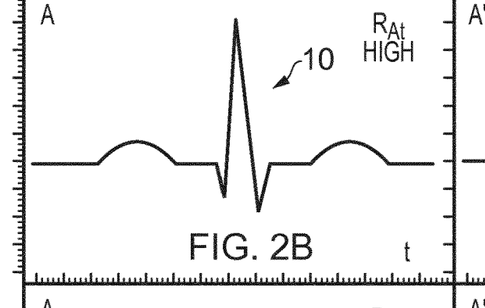
FIG. 2B illustrates an example of a high resolution signal.

FIG. 2B reproduces the ECG signal 10 using a high resolution amplitude scale (A) and a high resolution time scale (t). The resolution of the signal 10, $R_{At}$, is therefore high.

Figure 2C:
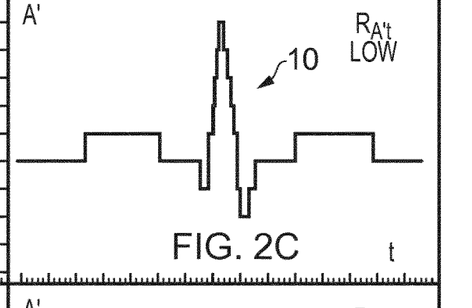
FIGS. 2C, 2D, 2E illustrate examples of low resolution signals.

FIG. 2C reproduces the ECG signal 10 using a low resolution amplitude scale (A') and a high resolution time scale (t). The resolution of the signal 10, $R_{A't}$, is therefore low.

Figure 2D:
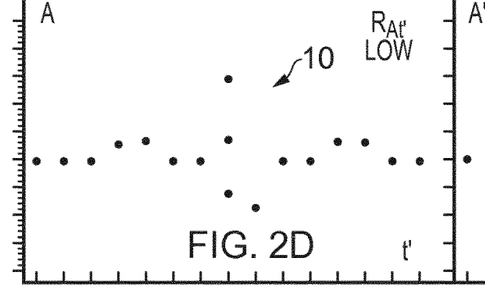

FIG. 2D reproduces the ECG signal 10 using a high resolution amplitude scale (A) and a low resolution time scale (t'). The resolution of the signal 10, $R_{At'}$, is therefore low.

Figure 2E:
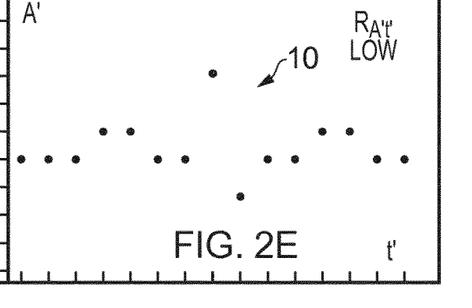

FIG. 2E reproduces the ECG signal 10 using a low resolution amplitude scale (A') and a low resolution time scale (t'). The resolution of the signal 10, $R_{A't'}$, is therefore low.

It should be noted that the high resolution amplitude scale (A) is dense compared to the sparse low resolution amplitude scale (A'). It should be noted that the high resolution time scale (t) is dense compared to the sparse low resolution time scale (t').

FIG. 2B illustrates a signal 10 that is a higher resolution signal. It would be saved as an amplitude value within a dense amplitude scale (A). The resolution of the saved signal 10, compared to the original signal, is to within a gradation of the scale (A) and is therefore high as the gradations are small.

FIGS. 2C and 2E illustrate examples of signals 10 that are lower resolution signals. If this is saved, it will be saved as an amplitude value within a sparse amplitude scale (A'). The resolution of the saved signal 10, compared to the original signal, is to within a gradation of the scale (A'). The gradations are large and the resolution of the saved signal 10 is therefore low.

The lower resolution signal (FIGS. 2C, 2E) has a low information content (entropy) compared to the higher resolution signal (FIG. 2B) and can therefore be stored and/or transmitted with less resources (e.g. band width).

The signal 10, illustrated in FIG. 2B, is saved as an amplitude value at a higher data rate. The higher data rate is indicated by the densely graduated time axis t. The resolution of the saved signal 10, compared to the original signal, is to within a gradation of the time axis t (associated with a higher data rate) and is therefore high.

The signal 10, as illustrated in FIGS. 2D and 2E, if it is saved is saved with an amplitude value at a lower data rate. The lower data rate is indicated by the sparsely graduated time axis t'. The resolution of the saved signal 10, compared to the original signal, is to within a gradation of the time axis t'(associated with the lower data rate) and is therefore low.

The lower resolution signals (FIGS. 2D and 2E) have low information content (entropy) compared to the higher resolution signal (FIG. 2B) and can therefore be stored and/or transmitted with less resources (e.g. band width).

Figure 3:
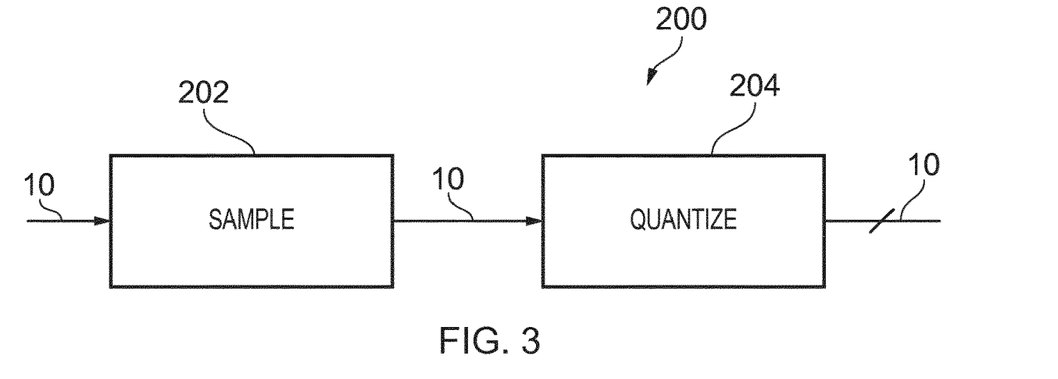
FIG. 3 illustrates an example of circuitry configured to sample and quantize the signal.

FIG. 3 illustrates an example of circuitry 200 that is configured to sample and quantize the signal 10. The signal 10 is sampled by sampler 202. The sampled signal 10 is then quantized by quantizer 204 to produce the digital signal 10 as an output.

Controlling the quantization (the density/sparsity of the amplitude scale) and data rate (the density/sparsity of the time scale) controls the resolution of the digital signal 10 produced by the circuitry 200.

The sampling rate of the sampler 202 may be constant or may be variable. According to the Nyquist-Shannon theorem, the data rate at which the sampler operates must be at least twice the highest frequency it is desired to reproduce in the digital signal 10.

In the example illustrated, the quantizer 204 is circuitry that quantizes the signal 10 irrespective of classification at block 102 of the method 100. The quantizing reduces the signal 10 to a number of significant bits. The higher resolution signal is then comprised of all of the significant bits including the most significant bits and the least significant bits. The lower resolution signal is comprised of a selected subset of the significant bits including the most significant bits but not including the least significant bits. In this way, it is therefore possible to use the same processing including sampling and quantization of the signal 10 but to change the amplitude resolution of the signal 10 by selecting fewer/more of the significant bits of the quantized signal 10.

If it is desired to change the resolution of the signal 10 in the time domain, then the circuitry 200 quantizes the signal 10 at a high data rate to produce the higher resolution signal and quantizes the signal 10 at a lower data rate to produce the lower resolution signal. This may be achieved by changing the sampling rate of the sampler 202, or it may be achieved by selecting only a subset of the samples produced by the sampler 202 for processing by the quantizer 204. For example, the higher resolution signal may be produced by processing every sample of the sampled signal 10 in the quantizer 204, whereas the lower resolution signal may be produced by processing every nth sample of the sampled signal 10 in the quantizer 204.

Figure 4:
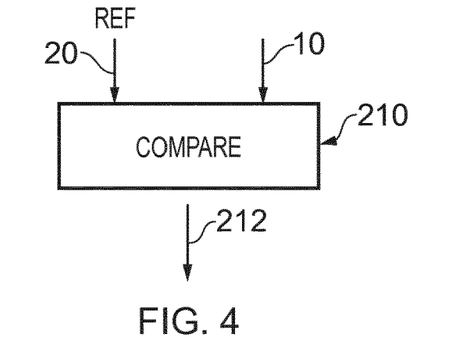
FIG. 4 illustrates an example of circuitry configured to classify a signal.

FIG. 4 illustrates an example of circuitry 210 that is configured to perform block 102 of the method 100. That is, it is configured to classify a signal 10.

In this example, the circuitry 210 is configured to classify a signal 10 by obtaining a measure of similarity between the signal 10 and a reference 20. In some but not necessarily all examples, the measure of similarity is obtained by comparing the signal 10 and the reference 20. The circuitry 210 produces an output 212 classifying the signal 10 as either anomalous or non-anomalous.

Where the reference 20 represents a normal (non-anomalous) signal, then the signal 10 is classified as an anomalous signal if it has a low measure of similarity and is classified as a non-anomalous signal if it has a high measure of similarity.

Where the reference 20 represents an anomalous signal (not-normal), then the signal 10 is classified as an anomalous signal if it has a high measure of similarity and is classified as a non-anomalous signal if it has a low measure of similarity.

The comparison may be performed by any suitable method. For example, it may be performed using correlation or it may be performed using a machine learning network such as a neural network.

The similarity measure may be determined by processing in the time domain only, by processing in the frequency domain only or by processing in both the time domain and the frequency domain.

The reference 20 may be fixed or dynamic. For example, it may represent an average of a preceding number of instances of the signal 10 measured for this subject. Alternatively, the reference 20 may be a standard reference that is used for all subjects.

It would normally be desirable to normalize the signal 10 with respect to the reference 20 before conducting the comparison. Such normalization may be achieved by feature matching a feature of the signal 10 to a feature of the reference 20. For example, in the example of the ECG signal 10 of FIG. 2A, the R-peak may be used. It may also be desirable to time align the signal 10 and the reference 20 before comparison. This may occur as a consequence of correlation or it may be performed separately by feature matching and time aligning the mapped features. For example, in the ECG signal 10 of FIG. 2A, the R-peak may be used to time align the signal 10 and the reference 20.

In the example of the circuitry 240 illustrated in FIG. 5, the comparison circuitry 210 is used to determine whether or not a signal 10 is anomalous or non-anomalous as previously described with reference to FIG. 4. The comparison circuitry 210 receives a reference 20 and the signal 10 and produces an output 212. If the output 212 indicates that the signal 10 is anomalous, the switch 232 directs the signal 10 for processing in accordance with the block 106 of the method 100. The anomalous signal is saved at a higher resolution as a higher resolution signal. If, however, the output 212 indicates that the signal 10 is non-anomalous then the switch 232 directs the signal 10 for processing in accordance with the block 108 of the method 100. The non-anomalous signal is saved at a lower resolution as a lower resolution signal or is not saved.

Figure 5:
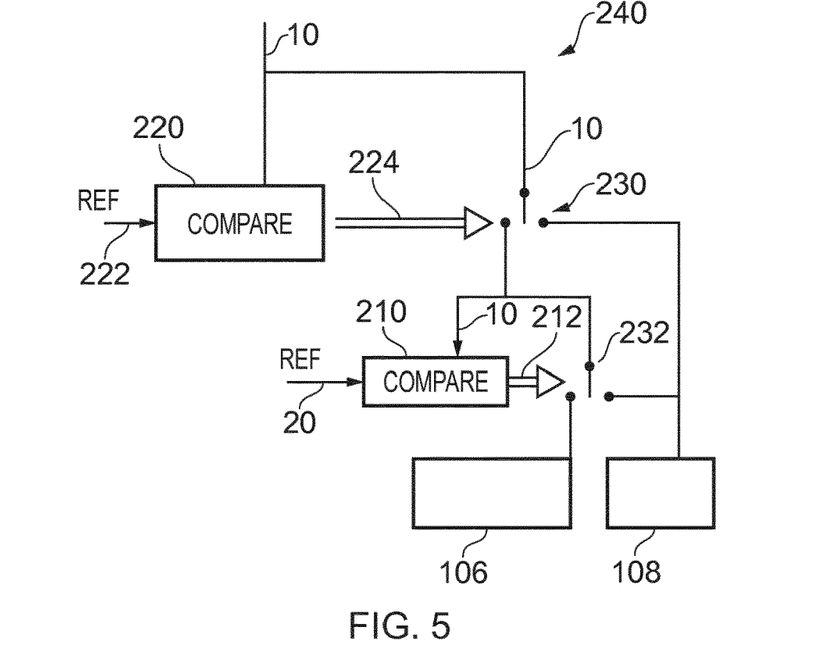
FIG. 5 illustrates an example of comparison circuitry.

The circuitry 240 illustrated in FIG. 5 additionally comprises comparison circuitry 220. The comparison circuitry 220 receives a reference 222 and the signal 10 and produces an output 224.

In this example, the circuitry 220 is configured to classify a signal 10 by obtaining a measure of similarity between the signal 10 and a reference 222. In some but not necessarily all examples, the measure of similarity is obtained by comparing the signal 10 and the reference 222. The circuitry 220 produces an output 224 classifying the signal 10 as either possibly anomalous or non-anomalous.

Where the reference 222 represents a normal (non-anomalous) signal, then the signal 10 is classified as a possibly anomalous signal if it has a low measure of similarity and is classified as a non-anomalous signal if it has a high measure of similarity.

Where the reference 222 represents an anomalous signal (not-normal), then the signal 10 is classified as possibly anomalous signal if it has a high measure of similarity and is classified as a non-anomalous signal if it has a low measure of similarity.

The comparison may be performed by any suitable method. For example, it may be performed using correlation or it may be performed using a machine learning network such as a neural network.

The similarity measure may be determined by processing in the time domain only, by processing in the frequency domain only or by processing in both the time domain and the frequency domain.

The reference 222 may be fixed or dynamic. For example, it may represent an average of a preceding number of instances of the signal 10 measured for this subject. Alternatively, the reference 222 may be a standard reference that is used for all subjects.

The reference 222 may be a low resolution version of the reference 20.

It would normally be desirable to normalize the signal 10 with respect to the reference 222 before conducting the comparison. Such normalization may be achieved by feature matching a feature of the signal 10 to a feature of the reference 222. It may also be desirable to time align the signal 10 and the reference 222 before comparison. This may occur as a consequence of correlation or it may be performed separately by feature matching and time aligning the mapped features.

If the output 224 indicates that the signal 10 is non-anomalous, the switch 230 directs the signal 10 for processing in accordance with the block 108 of the method 100. The non-anomalous signal is saved at a lower resolution as a lower resolution signal or is not saved.

If the output 224 indicates that the signal 10 is possibly anomalous, the switch 230 directs the signal 10 for processing by comparison circuitry 210.

The purpose of the comparison circuitry 220 is to identify a portion of an incoming signal 10 that is likely to be or has a possibility of being an anomalous signal. Referring back to the example of FIG. 2A, for example, this comparison circuitry 220 may only direct a portion of the signal 10 to the comparison circuitry 210 if it determines that there is likely to be a PQRST complex within that portion of the signal 10 and otherwise directs the signal 10, via the switch 230, to be processed as a non-anomalous signal in accordance with block 108.

The comparison circuitry 210 in FIG. 5 is therefore configured to classify a signal 10 by obtaining a measure of similarity between the signal 10 and a reference 20 by comparison of a portion of the signal 10 and a portion of the reference 20 wherein the portion of the signal 10 and the portion of the reference 20 are determined from a comparison of the reference 222 and the signal 10 at comparison circuitry 220. In this way, the circuitry illustrated in FIG. 5 is configured to control saving of the signal 10 to memory with a conditional resolution by saving only the portion of the signal 10 that is classified as anomalous at a higher resolution.

In the example of the ECG signal 10 of FIG. 2A, the comparison made by the comparison circuitry 210 is therefore limited to a small region about a detected feature (e.g. the R-peak).

The reference 222 and the reference 20 may be the same or they may be different. For example, the comparison that occurs at comparison circuitry 220 may be at a lower resolution than the comparison that occurs at the comparison circuitry 210. Consequently, the reference 222 may be a low resolution reference and the reference 20 may be a high resolution reference.

Figure 6:
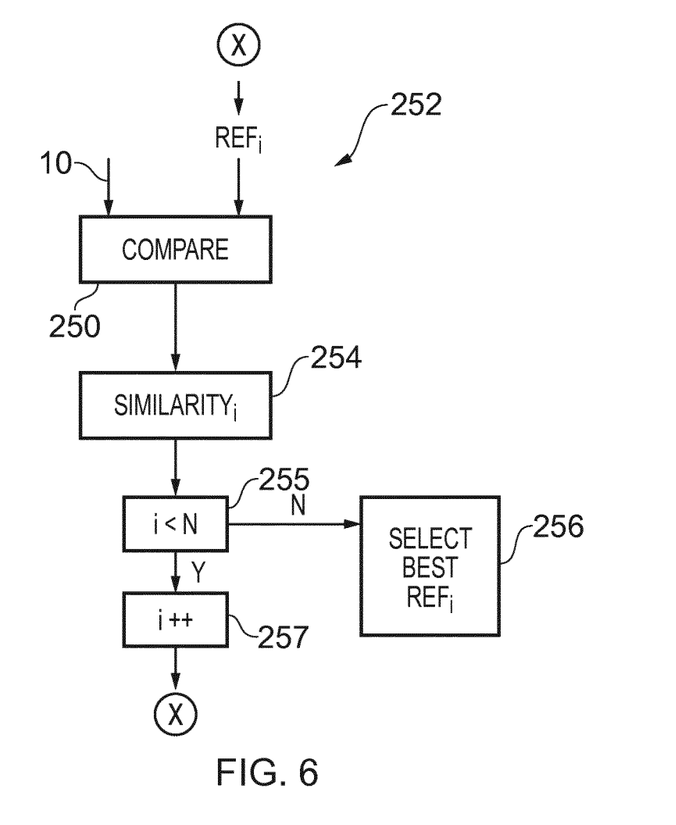
FIG. 6 illustrates an example of tiered comparison circuitry.

FIG. 6 schematically illustrates operation of circuitry 252. The circuitry 252 is configured to determine the reference 20, 222 used in a comparison. This circuitry is configured to compare each putative reference $REF_i$ in a set of putative references $\{REF_i; 1 \leq i \leq N\}$ with the signal 10, identifying the putative reference that best matches the signal 10 as the reference to be used. At block 250, the putative reference $REF_i$ is compared with the signal 10. A similarity measure is determined for that index value i at block 254. If there are more putative references remaining (255) then the index is increased by 1 (257) and the comparison at block 250 is repeated with the next putative reference $REF_i$. If all of the putative references $REF_i$ in this set of putative references $\{REF_i\}$ have been compared and similarity indexes determined, then the method branches to block 256 where the best reference is determined based on the best similarity value.

The similarity value may be determined by a correlation between the putative reference $REF_i$ and the signal 10. The best match may be determined by the putative reference $REF_i$ with the highest correlation or the highest correlation for a particular percentage of the signal 10.

In some but not necessarily all examples, the comparison of each putative reference $REF_i$ in the set of putative references $REF_i$ with the signal 10 to identify the reference 20 is at a lower resolution than the comparison 210 of the signal 10 and the reference 20 to obtain the measurement of similarity used to determine whether or not a signal is or is not anomalous.

Figure 7:
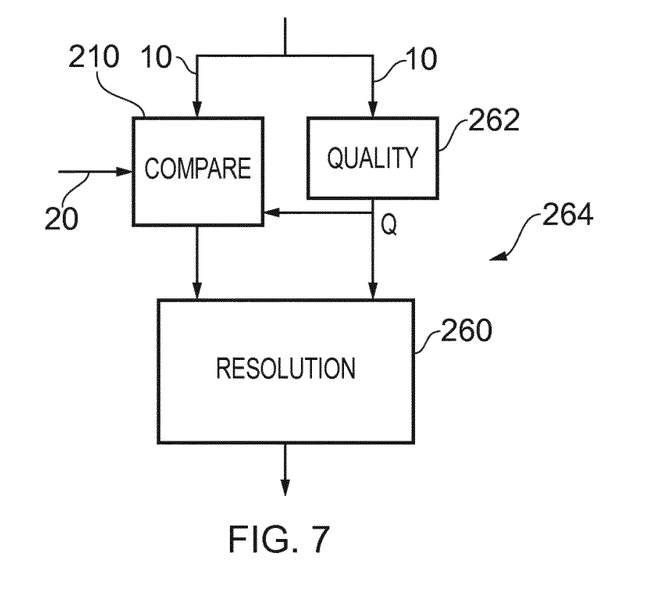
FIG. 7 illustrates an example of circuitry configured to measure a quality value of the signal.

FIG. 7 illustrates circuitry 262 that is configured to measure a quality value Q of the signal 10. The quality of the signal 10 may be assessed in a number of different ways. It may, for example, be obtained by measuring a variance between different instances of the signal 10 at different times, when the signal 10 is cyclic and repetitive.

In this example, the circuitry 264 is configured to classify the signal 10 in dependence upon the measure of quality of the signal 10. In this example, the comparison circuitry 210 receives the quality value Q. If the quality value Q is above a predetermined threshold, then the comparison circuitry 210 is able to identify the signal 10 as anomalous. If, however, the quality value is below the threshold, then the comparison circuitry 210 is not capable of identifying the signal 10 as anomalous. A consequence of this is that only high quality anomalous signals are saved at higher resolutions.

A 'higher resolution' may be a high enough resolution to classify the signal as anomalous. The resolution may be increased or decreased based on the anomaly or expected anomaly.

A further development of this is illustrated in FIG. 7. The circuitry 260 is configured to determine the resolution at which an anomalous signal is saved based upon the quality value Q. Thus an anomalous signal that has a quality value above a threshold value may be saved and the resolution at which it is saved may increase based upon an increasing quality value of the signal. In this way, there is no attempt to store an anomalous signal at a resolution that significantly exceeds its quality.

Figure 8:
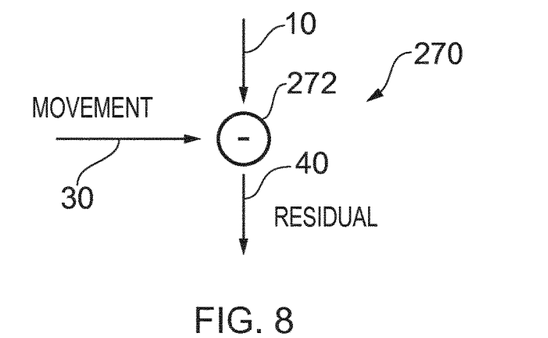
FIG. 8 illustrates an example of circuitry configured to compensate for movement artefacts affecting the signal.

FIG. 8 illustrates an example of circuitry 270 that is configured to compensate for movement artefacts affecting the signal 10. In this example, a compensator 272 subtracts the movement artefact 30 from the signal 10 to produce a residual signal 40. The residual signal 40 is then used as a replacement for the signal 10. In this example, the compensation removes the movement artefact from the signal 10. In other examples, the compensation circuitry 270 may flag a signal 10 as unreliable because of movement.

The movement artefact 30 may be subtracted from the signal 10 in the time domain and/or the frequency domain depending upon application.

In the example of the ECG signal 10 illustrated in FIG. 2A, it is unlikely that the cycle of the ECG signal 10 and the cycle of a movement artefact caused by respiration will be synchronized. It is likely that they will have different periods. It is therefore possible by analyzing the signal 10 outside the PQRST complex to identify a contribution to the signal 10 from respiration. This may be achieved by integration over an extended period of time. Having a model for the respiration artefact caused by movement, it is possible to subtract the artefact 30 from the signal 10 to produce the residual 40.

Figure 9A:
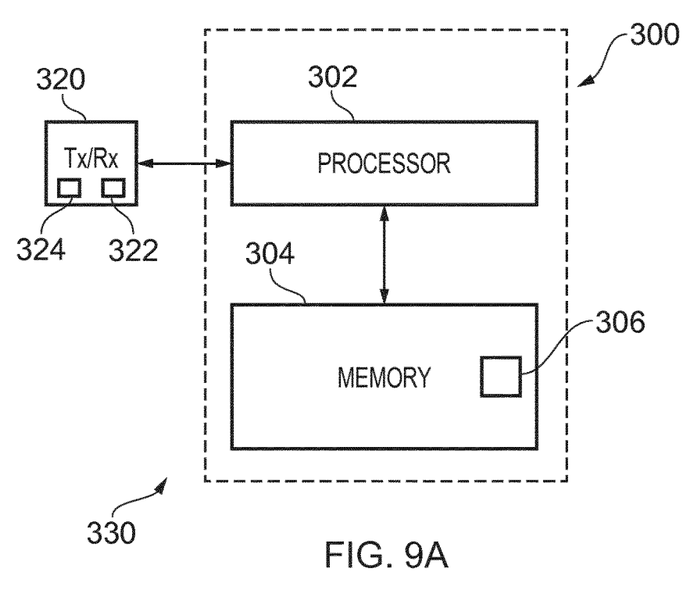
FIG. 9A illustrates an example of an apparatus.

The circuitry described in the preceding examples may be provided in an apparatus 330, for example as illustrated in FIG. 9A. In this example, the circuitry is provided by a controller 300. Implementation of a controller 300 may be as controller circuitry. The controller 300 may be implemented in hardware alone, have certain aspects in software including firmware alone or can be a combination of hardware and software (including firmware).

As illustrated in FIG. 9A the controller 300 may be implemented using instructions that enable hardware functionality, for example, by using executable instructions of a computer program 306 in a general-purpose or special-purpose processor 302 that may be stored on a computer readable storage medium (disk, memory etc) to be executed by such a processor 302.

The processor 302 is configured to read from and write to the memory 304. The processor 302 may also comprise an output interface via which data and/or commands are output by the processor 302 and an input interface via which data and/or commands are input to the processor 302.

The memory 304 stores a computer program 306 comprising computer program instructions (computer program code) that controls the operation of the apparatus 330 when loaded into the processor 302. The computer program instructions, of the computer program 306, provide the logic and routines that enables the apparatus to perform the methods illustrated in FIGS. 1 to 8. The processor 302 by reading the memory 304 is able to load and execute the computer program 306.

The computer program 306 is program, that when run on a processor 302, enables the processor 302 to control: saving of a signal 10 with conditional resolution in dependence upon a classification of the signal 10, wherein an anomalous signal is saved at higher resolution as a higher resolution signal and a non-anomalous signal is saved at lower resolution as a lower resolution signal or not saved.

A 'higher resolution' may be a high enough resolution to classify the signal as anomalous.

Figure 9B:
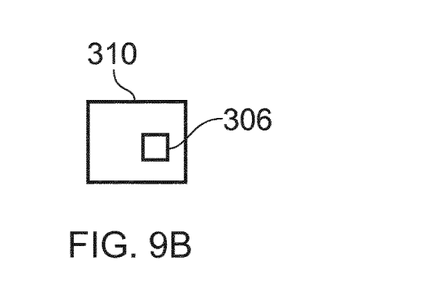
FIG. 9B illustrates an example of a delivery mechanism for a computer program.

The apparatus 330 therefore comprises:
at least one processor 302; and
at least one memory 304 including computer program code the at least one memory 304 and the computer program code configured to, with the at least one processor 302, cause the apparatus 330 at least to perform:
causing classifying of a signal 10; and
controlling saving of the signal 10 with conditional resolution in dependence upon classification of the signal 10
wherein an anomalous signal is saved at higher resolution as a higher resolution signal and a non-anomalous signal is saved at lower resolution as a lower resolution signal or not saved As illustrated in FIG. 9B, the computer program 306 may arrive at the apparatus 330 via any suitable delivery mechanism 310. The delivery mechanism 310 may be, for example, a non-transitory computer-readable storage medium, a computer program product, a memory device, a record medium such as a compact disc read-only memory (CD-ROM) or digital versatile disc (DVD), an article of manufacture that tangibly embodies the computer program 306. The delivery mechanism may be a signal configured to reliably transfer the computer program 306. The apparatus 330 may propagate or transmit the computer program 306 as a computer data signal.

Although the memory 304 is illustrated as a single component/circuitry it may be implemented as one or more separate components/circuitry some or all of which may be integrated/removable and/or may provide permanent/semi-permanent/dynamic/cached storage.

Although the processor 302 is illustrated as a single component/circuitry it may be implemented as one or more separate components/circuitry some or all of which may be integrated/removable. The processor 302 may be a single core or multi-core processor.

The apparatus 330 comprises in addition to the controller 300, a wireless transmitter module 320. In this example, the wireless transmitter module 320 comprises a wireless transmitter 324 and data compression circuitry 322 configured for data compression of the saved signal 10 before wireless transmission of the compressed saved signal 10 via the wireless transmitter 324. The signal 10 may be saved to memory 304. In some examples, the wireless transmitter 324 is provided by a cellular radio transceiver.

Figure 10:
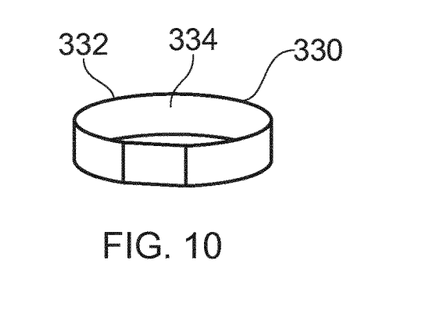
FIG. 10 illustrates another example of an apparatus.

FIG. 10 illustrates an example of the apparatus 330 configured as a personal, wearable device 332. The apparatus 330 comprises one or more sensors 334 for sensing the signal 10.

In this example, the personal, wearable device 332 is a strap that may be worn around a limb or may be worn around a torso.

References to 'computer-readable storage medium', 'computer program product', 'tangibly embodied computer program' etc. ora 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software fora programmable processor or firmware such as, for example, the programmable content of a hardware device whether instructions for a processor, or configuration settings for a fixed-function device, gate array or programmable logic device etc.

As used in this application, the term 'circuitry' refers to all of the following:
 (a) hardware-only circuit implementations (such as implementations in only analog and/or digital circuitry) and
 (b) to combinations of circuits and software (and/or firmware), such as (as applicable):
  (i) to a combination of processor(s) or (ii) to portions of processor(s)/software (including digital signal processor(s)), software, and memory(ies) that work together to cause an apparatus, such as a mobile phone or server, to perform various functions and
 (c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

The blocks illustrated in the FIGS. 1 to 8 may represent steps in a method and/or sections of code in the computer program 306. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
 at least one processor; and
 at least one memory including computer program code,
 the at least one memory and the computer program code configured to, with the at least one processor, cause the apparatus at least to perform:
 classifying an electrocardiogram signal as anomalous or non-anomalous;
 generating an output signal based on the classified electrocardiogram signal;
 controlling operation of a switch of a circuit in the apparatus using the output signal;
 obtaining a measure of similarity between the electrocardiogram signal and a reference signal by comparison of the electrocardiogram signal and the reference signal, wherein the electrocardiogram signal is classified as an anomalous signal or as a non-anomalous signal based on the measure of similarity, and wherein the signal is classified as an anomalous signal if it has a lower measure of similarity and is classified as a non-anomalous signal if it has a higher measure of similarity;
 controlling saving of the electrocardiogram signal with a conditional resolution in dependence upon the classification of the electrocardiogram signal as anomalous or non-anomalous;
 and
 saving the electrocardiogram signal at higher resolution as a higher resolution signal when the electrocardiogram signal is classified as anomalous,
 wherein the controlling comprises controlling operation of the switch to direct the electrocardiogram signal to another switch of the circuit in the apparatus to be saved at the higher resolution as the higher solution signal when the output signal indicates the electrocardiogram signal is anomalous, and wherein the controlling comprises controlling operation of the switch to direct the electrocardiogram signal to be saved at a lower resolution as a lower resolution signal or to be not saved when the output signal indicates the electrocardiogram signal is non-anomalous.

2. The apparatus as claimed in claim 1, wherein the at least one memory and the computer program code are configured to, with the at least one processor, cause the apparatus at least to further perform:
quantizing the electrocardiogram signal irrespective of classification into a number of significant bits,
wherein the higher resolution signal is comprised of the number of significant bits including most significant bits and least significant bits, and
wherein the lower resolution signal is comprised of a selected sub-set of the number of significant bits including most significant bits but not including least significant bits.

3. The apparatus as claimed in claim 1, wherein the at least one memory and the computer program code are configured to, with the at least one processor, cause the apparatus at least to further perform:
quantizing the electrocardiogram signal irrespective of classification at a data rate,
wherein the higher resolution signal comprises quantized samples at the data rate, and
wherein the lower resolution signal comprises quantized samples selected at a rate less than the data rate.

4. The apparatus as claimed in claim 1,
wherein the measure of similarity between the electrocardiogram signal and the reference signal is obtained by comparison of a portion of the electrocardiogram signal and a portion of the reference signal,
wherein the portion of the electrocardiogram signal and the portion of the reference signal are determined from a comparison of the reference signal and the electrocardiogram signal, and
wherein controlling saving of the electrocardiogram signal with the conditional resolution comprises saving only the portion of the electrocardiogram signal that is classified as anomalous at higher resolution.

5. The apparatus as claimed in claim 4, wherein classifying the electrocardiogram signal comprises comparing the reference signal and the electrocardiogram signal to determine the portion of the electrocardiogram signal and a portion of the reference signal at the lower resolution than comparison of the electrocardiogram signal and the reference signal to obtain the measure of similarity.

6. The apparatus as claimed in claim 1, wherein classifying the electrocardiogram signal comprises determining the reference signal by comparison of each putative reference in a set of putative references with the electrocardiogram signal, identifying the putative reference that best matches the electrocardiogram signal as the reference signal.

7. The apparatus as claimed in claim 1, wherein classifying the electrocardiogram signal comprises classifying the electrocardiogram signal in dependence upon a measure of quality of the electrocardiogram signal.

8. The apparatus as claimed in claim 1, wherein controlling saving of the electrocardiogram signal comprises saving the electrocardiogram signal, when classified as anomalous, with the higher resolution that is dependent upon the quality of the electrocardiogram signal.

9. The apparatus as claimed in claim 1, wherein the at least one memory and the computer program code are configured to, with the at least one processor, cause the apparatus at least to further perform:
compensating for movement artefacts affecting the electrocardiogram signal.

10. The apparatus as claimed in claim 1, wherein the electrocardiogram signal is a cyclic bio signal.

11. The apparatus as claimed in claim 1, wherein the at least one memory and the computer program code are configured to, with the at least one processor, cause the apparatus at least to further perform:
normalizing the electrocardiogram signal by feature matching the Rpeak feature of the electrocardiogram signal to a feature of the reference signal; and
causing the electrocardiogram signal and the reference signal to be time aligned before comparison.

12. The apparatus as claimed in claim 11, wherein the at least one memory and the computer program code are configured to, with the at least one processor, cause the apparatus at least to further perform:
analyzing the electrocardiogram signal outside the PQRST complex to identify a movement artefact in the electrocardiogram signal caused by respiration.

13. The apparatus as claimed in claim 1, wherein controlling saving of the electrocardiogram signal comprises saving the electrocardiogram signal with the higher resolution only when the electrocardiogram signal is classified as anomalous.

14. The apparatus as claimed in claim 1 comprising:
a transmitter, and wherein the at least one memory and the computer program code are configured to, with the at least one processor, cause the apparatus at least to further perform:
data compressing the saved signal before transmission of the compressed saved signal via the transmitter.

15. The apparatus as claimed in claim 1, wherein the apparatus is wearable by a user, and further comprises one or more sensors for sensing the electrocardiogram signal.

16. The apparatus as claimed in claim 15, wherein the apparatus is configured as a strap that is wearable by the user.

17. A method comprising:
classifying an electrocardiogram signal as anomalous or non-anomalous;
generating an output signal based on the classified electrocardiogram signal;
controlling operation of a switch of a circuit in a controller using the output signal;
obtaining a measure of similarity between the electrocardiogram signal and a reference signal by comparison of the electrocardiogram signal and the reference signal, wherein the electrocardiogram signal is classified as an anomalous signal or as a non-anomalous signal based on the measure of similarity, and wherein the signal is classified as an anomalous signal if it has a lower measure of similarity and is classified as a non-anomalous signal if it has a higher measure of similarity; and
controlling saving of the electrocardiogram signal with conditional resolution in dependence upon the classification of the electrocardiogram signal as anomalous or non-anomalous;
and
saving the electrocardiogram signal at higher resolution as a higher resolution signal when the electrocardiogram signal is classified as anomalous, wherein the controlling comprises controlling operation of the switch to direct the electrocardiogram signal to another switch of the circuit in the controller to be saved at the higher resolution as the higher solution signal when the output signal indicates the electrocardiogram signal is anomalous, and wherein the controlling comprises controlling operation of the switch to direct the electrocardiogram signal to be saved at a lower resolution as a lower resolution signal or to be not saved when the output signal indicates the electrocardiogram signal is non-anomalous.

18. A computer program, embodied on a non-transitory computer readable medium and executable by a processor, wherein, the computer program, when executed by the processor of a controller, causes the processor to:

classify an electrocardiogram signal as anomalous or non-anomalous;

generate an output signal based on the classified electrocardiogram signal;

control operation of a switch of a circuit in the controller using the output signal;

obtain a measure of similarity between the electrocardiogram signal and a reference signal by comparison of the electrocardiogram signal and the reference signal, wherein the electrocardiogram signal is classified as an anomalous signal or as a non-anomalous signal based on the measure of similarity, and wherein the signal is classified as an anomalous signal if it has a lower measure of similarity and is classified as a non-anomalous signal if it has a higher measure of similarity; and control saving of the electrocardiogram signal with a conditional resolution in dependence upon the classification of the electrocardiogram signal as anomalous or non-anomalous;

and save the electrocardiogram signal at higher resolution as a higher resolution signal when the electrocardiogram signal is classified as anomalous, wherein the control comprises controlling operation of the switch to direct the electrocardiogram signal to another switch of the circuit in the controller to be saved at the higher resolution as the higher solution signal when the output signal indicates the electrocardiogram signal is anomalous, and wherein the control comprises controlling operation of the switch to direct the electrocardiogram signal to be saved at a lower resolution as a lower resolution signal or to be not saved when the output signal indicates the electrocardiogram signal is non-anomalous.

* * * * *